United States Patent [19]

von Bittera et al.

[11] Patent Number: 4,623,346

[45] Date of Patent: Nov. 18, 1986

[54] ISOBUTYLENE POLYMER ACTIVE COMPOUND RELEASE SYSTEMS

[75] Inventors: Miklos von Bittera, Leverkusen; Rolf Dhein, Krefeld; Rolf-Volker Meyer, Krefeld; Roland Rupp, Leichlingen, all of Fed. Rep. of Germany

[73] Assignee: Bayer Aktiengesellschaft, Leverkusen, Fed. Rep. of Germany

[21] Appl. No.: 675,160

[22] Filed: Nov. 27, 1984

[30] Foreign Application Priority Data

Dec. 10, 1983 [DE] Fed. Rep. of Germany ....... 3344691

[51] Int. Cl.⁴ .................... A61K 9/60; A61K 9/70; A61L 15/00
[52] U.S. Cl. ................................. 604/896; 604/897
[58] Field of Search ................. 428/156; 604/897, 896

[56] References Cited

U.S. PATENT DOCUMENTS

| | | | |
|---|---|---|---|
| 3,996,934 | 12/1976 | Zafforoni | 604/897 |
| 4,031,894 | 6/1977 | Urguhart et al. | 604/386 |
| 4,201,211 | 5/1980 | Chandrasekoran et al. | 604/897 |
| 4,455,146 | 6/1984 | Noda et al. | 604/897 |

FOREIGN PATENT DOCUMENTS 56-2909  1/1981  Japan ....................... 604/897

*Primary Examiner*—Allan Lieberman
*Attorney, Agent, or Firm*—Sprung Horn Kramer & Woods

[57] ABSTRACT

In a therapeutic system such as a plaster for administration of an active compound through the skin and comprising a covering layer which is essentially impermeable to the active compound an active compound reservoir layer and a protective layer which can be pulled off and which is essentially impermeable to the active compound, the improvement wherein the reservoir layer contains about 1–30% of active compound in an elastomer mixture comprising at least one of polyisobutylene, polybutadiene oil and paraffin oil, and a tackifying resin. Thereby the active compound can be released in regulated relatively large quantity over a prolonged period of time.

12 Claims, 6 Drawing Figures

ISOBUTYLENE POLYMER ACTIVE COMPOUND RELEASE SYSTEMS

The invention relates to a system for the release of an active compound to the skin over a prolonged period, in particular to antiphlogistic medicinal plasters.

U.S. Pat. No. 4,031,894 describes medicinal plasters which have a reservoir of mineral oil and polyisobutene. The polyisobutene is a mixture of components of various molecular weights, in particular polyisobutenes of molecular weight 35,000–50,000 and 1,000,000–1,500,000.

This plaster is only suitable for active compounds which have to be applied in very low doses. Scopolamine is mentioned in the U.S. patent specification.

An object of the present invention is therefore to develop medicinal plasters, with the aid of which regulated larger, therapeutically effective amounts of an active compound can be administered via the skin over a prolonged period. These plasters should be particularly suitable for the administration of antiphlogistics. They should be compatible with the skin, and with the aid of these plasters it should be possible to administer high therapeutically effective doses of the active compound.

Known active compound release systems, such as, for example, gels, ointments, plasters and the like, allow only limited absorption of the active compound through the skin. The absorption depends on the base and on the properties of the active compounds.

It has now been found that therapeutic systems which contain the active compound in a reservoir layer which, as the polymer, contains polyisobutylenes and/or particular copolymers of isobutylene, which in each case have a defined molecular weight distribution, are particularly suitable for this purpose.

The present invention thus relates to a therapeutic system for the application of an active compound to the skin, containing a covering layer, a reservoir layer and a protective layer which can be pulled off, the reservoir layer containing a polymer consisting of polyisobutylene and/or copolymers thereof, an entraining agent and a resin.

Preferably the active compound-containing reservoir consists of 30–60% by weight of polymer, 30–60% by weight of entraining agent and 2–40% by weight of a resin, the three components adding up to 100% by weight.

Polymers in the context of the present invention are understood as meaning polyisobutylenes and/or copolymers thereof.

Polyisobutylenes in the context of the invention are understood as meaning polyisobutylenes which have a molecular weight distribution $M_w/M_n$ of 1.5 to 3.5, preferably 2.0 to 3.0, resulting from the preparation method, and a viscosity average molecular weight—again resulting from the preparation method—of 30,000 to 4,000,000 g/mol. The viscosity average of the polyisobutylenes to be used according to the invention is preferably 50,000 to 1,000,000 g/mol, and particularly preferably 80,000 to 500,000 g/mol. The viscosity average can be determined in a known manner as described in Polymer Handbook, J. Brandrup and F. H. Immergut, Wiley & Sons, New York, 1975, chapter IV, page 35.

These polyisobutylenes have been known for a long time and can be prepared, for example, with acid catalysts as described in U.S. Pat. No. 2,203,873 or German Reichspatent No. 704,038.

Copolymers of isobutylene in the context of the invention are those of isobutylene with 0.5–5 mol % of conjugated diolefins, preferably those with 4–6 C atoms, such as, for example, buta-1,3-diene, piperylene and 2,3-dimethylbutadiene, and particularly preferably with isoprene, the molecular weight of which can be from 30,000 to 200,000 g/mol. These isobutene copolymers are also known. Polyisobutylene homopolymers with a viscosity average of 80,000 to 500,000 are especially preferably used.

Entraining agents in the context of the present invention are understood as meaning oils, fatty acid esters, triglycerides, alcohols and/or fatty acids.

Oils in the context of the present invention are understood as meaning high-boiling aliphatic, araliphatic and/or aromatic hydrocarbons, preferably paraffin oil, Purcellin oil, perhydrosqualene and solutions of microcrystalline waxes in the oils, and mineral oils, preferably oils with a boiling range between 150° C. and 400° C.; and furthermore unsaturated hydrocarbons with at least 16 C atoms, such as, for example, oligomers of monoolefins, such as tetraisobutylene, pentaisobutylene and hexaisobutylene, or liquid polymers of diene(monoene)(co)polymers. Examples of liquid polymers of conjugated dienes are those of butadiene, isoprene, penta-1,3-diene, 2,3-dimethylbutadiene, copolymers of various dienes and liquid copolymers of a conjugated diolefin and small amounts of monoolefins, such as, for example, but-1-ene, isobutene, hex-1-ene, oct-1-ene and styrene, with molecular weights of 400 to 6,000, preferably 800 to 3,000, iodine numbers of 200 to 500 and viscosities of 100–10,000 cP at 50° C.

Liquid polybutadiene polymers which are at least 90% 1,4-linked, in which the content of cis-double bonds is more than 60% and which have molecular weights of 1,000 to 4,000 are particularly preferred.

Oils are also understood as meaning silicone oils of various viscosities, preferably with average molecular weights of 312 to 15,000, particularly preferably polydimethylsiloxanes.

Fatty acid esters are understood as meaning those which contain at least 12 C atoms, preferably 15 to 46 C atoms and particularly preferably 16 to 36 C atoms. By these there are understood, in particular: ethyl stearate, hexyl laurate, dipropylene glycol pelargonate, cetyl palmitate, isopropyl myristate, isopropyl palmitate, caprylic/capric acid esters of saturated fatty alcohols of $C_{12}$–$C_{18}$ chain length, isopropyl stearate, oleyl oleate, decyl oleate, ethyl oleate and synthetic duck uropygial gland fat, in each case individually or as a mixture.

Triglycerides are understood as meaning pure or mixed esters of glycerol and fatty acids of $C_8$–$C_{18}$ chain length, preferably caprylic and/or capric acid triglycerides.

Fatty acids are understood as meaning saturated or unsaturated fatty acids, preferably those with 12–24 C atoms, by themselves or as mixtures with one another, particularly preferably oleic acid.

Oils in the context of the invention are furthermore understood as meaning: sweet almond oil, avocado oil, sesame oil, castor oil, olive oil, grape seed oil, clove oil, groundnut oil, corn oil, hazelnut oil, jojoba oil, carthama oil and wheatgerm oil, in each case by themselves or as a mixture.

Resins in the context of the present invention are understood as meaning rosin, dehydrogenated rosin, glycerol esters of dehydrogenated rosin, glycerol esters of rosin gum, hydrogenated rosin, glycerol esters of hydrogenated rosin, pentaerythritol esters of hydrogenated rosin, methyl esters of hydrogenated rosin, polymerized rosin, glycerol esters of polymerized rosin, terpene resins, coumarone/indene resins, hydrogenated petroleum resins, rosin modified by maleic anhydride and rosin derivatives, $C_5$-petroleum resins and half-esters of styrene/maleic acid copolymers, by themselves or as mixtures with one another. Polyterpene resins of alpha- or beta-pinene or modified glycerol esters of rosin are particularly preferred. Depending on the properties required in respect of tackiness and adhesion to the part onto which the resulting plaster is to be applied, these resins can be used either by themselves or in combination with one another.

Antipholgistics in the context of the present invention are one or more antiphlogistics of the general formula I and/or II.

Antiphlogistics of the general formula I have the following structure:

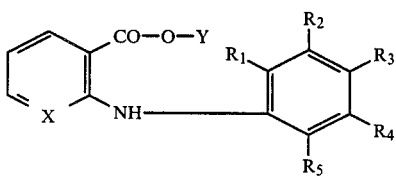

wherein
$R_1$–$R_5$ can be identical or different and denotes hydrogen, halogen, lower alkyl or substituted alkyl,
X denotes N or CH and
Y denotes hydrogen, metal ions, alkyl or substituted alkyl.

Halogen denotes fluorine, chlorine or bromine, preferably chlorine and/or bromine and particularly preferably chlorine. Lower alkyl is preferably alkyl with 1–6 C atoms, particularly preferably 1–4 C atoms, and substituted alkyl $R_1$–$R_5$ preferably denotes trihalogenoalkyl, particularly preferably trifluoromethyl. Metal ions are understood as meaning the ions of alkali metals, alkaline earth metals or aluminum preferably sodium. Substituted alkyl Y preferably denotes alkoxyalkyl, hydroxyalkyl, hydroxyalkoxyalkyl or trihalogenoalkyl, in which the number of C atoms is 1 to 6 and the alkyl chain can be straight or branched.

Antiphlogistics which are preferably used are those of the general formula I in which
$R_3$ and $R_4$ denote hydrogen,
X denotes nitrogen or a CH group,
Y denotes hydrogen, $C_1$–$C_4$-alkyl or substituted $C_1$–$C_4$-alkyl, hydroxyalkyl or hydroxyalkoxyalkyl with 1 to 6 C atoms and
$R_1$, $R_2$ and $R_5$ denote hydrogen, chlorine, $C_1$–$C_4$-alkyl or trifluoromethyl.

Particularly preferred antiphlogistics of the general formula I are those in which
X represents a CH group,
Y denotes hydrogen or hydroxyalkoxyalkyl with 1 to 6 C atoms and
$R_1$, $R_2$ and $R_5$ denote methyl, hydrogen, trifluoromethyl or chlorine.

The following antiphlogistics are very particularly preferred:

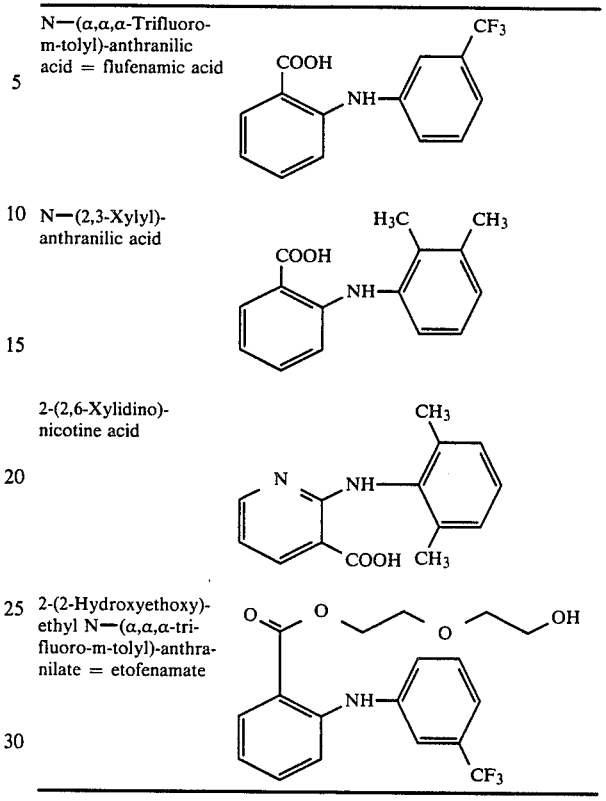

Antiphlogistics in the context of the present invention are furthermore antiphlogistics of the general formula II having the structure:

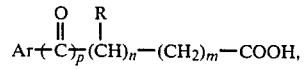

in which
R denotes hydrogen, lower alkyl or substituted alkyl,
Ar denotes aryl, heteroaryl, substituted aryl or substituted heteroaryl,
n+m denote an integer and have the value zero, 1 or 2, and
p denotes zero or 1,
with the condition that Ar does not denote aryl or heteroaryl if n, m and p have the value of zero, and esters or amides thereof.

R preferably denotes lower alkyl radicals with 1–6 C atoms, preferably 1–4 C atoms, substituted alkyl, alkoxyalkyl or trihalogenoalkyl; aryl or heteroaryl, for example phenyl, naphthyl, thiophenyl, pyrrolyl, indenyl, indolyl, benzothiazinyl or phenothiazinyl.

Substituents for aryl or heteroaryl are alkyl, preferably straight-chain or branched alkyl with up to 6 C atoms, alkoxy, hydroxyalkyl, acyl, hydroxyl, acetoxy, benzoyl, substituted benzoyl, phenyl, substituted phenyl, phenoxy, halogen, phenylalkenyl and phenylalkyl.

The esters are alkyl esters with 1–6 C atoms, preferably 1–4 C atoms in the alcohol component, particularly preferably methyl, ethyl, i- and n-propyl, substituted alkyl, for example β-hydroxyethyl, esters of glycolic acid. The amides can also contain lower alkyl or substituted alkyl radicals in the grouping —CO—NH₂ instead of one or both of the amide hydrogens.

The following antiphlogistics of the general formula II are particularly preferred:

| | |
|---|---|
| 2-Hydroxybenzoic acid | 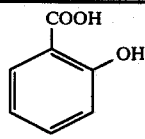 |
| 2-Acetoxybenzoic acid | 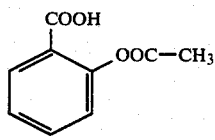 |
| 2',4'-Difluoro-4-hydroxy-3-biphenylcarboxylic acid | 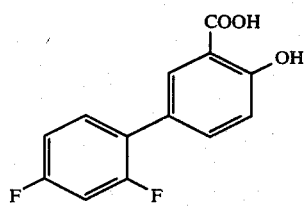 |
| 2-Hydroxybenzamide | 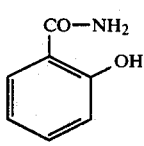 |
| [2-(aminocarbonyl)phenoxy]-acetic acid | 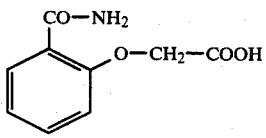 |
| 4-Allyloxy-3-chlorophenyl-acetic acid = alclofenac | 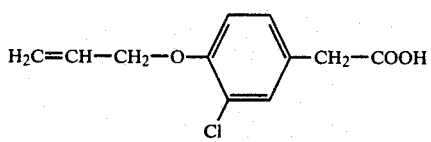 |
| 2-[(2,6-Dichlorophenyl)amino]-2-(4-Chlorophenyl)-αacid | 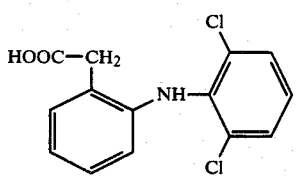 |
| 10-Methyl-phenothiazin-2-yl-acetic acid = metiazinic acid | 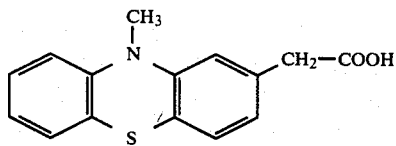 |
| 1-Methyl-5-(p-toluoly)-pyrrol-2-yl-acetic acid | 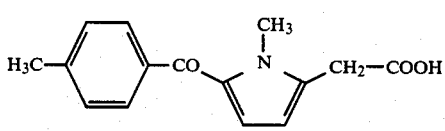 |
| D-2(6-Methoxy-2-naphthyl)-propionic acid = naproxen | 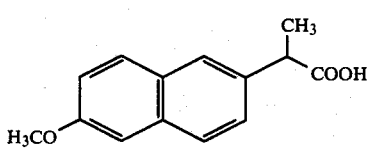 |

| | |
|---|---|
| 2-(p-Isobutylphenyl)-propionic acid | 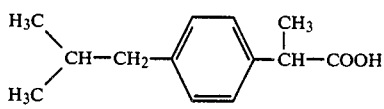 |
| 2-(3-Phenoxyphenyl)-propionic acid | 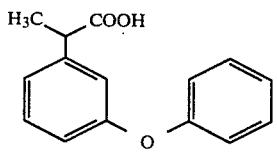 |
| 2-(m-Benzoylphenyl)-propionic acid = ketoprofen | 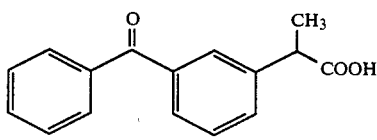 |
| 2-[4-(1-Oxo-2-isoindolinyl)-phenyl]-propionic acid = indoprofen | 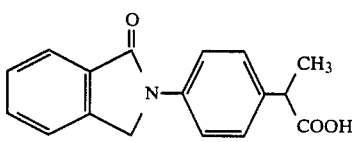 |
| 2-(2-Fluorobiphenyl-4-yl)-propionic acid | 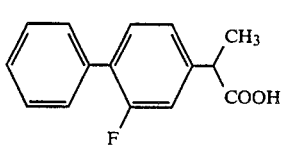 |
| 3-(4-Biphenylcarbonyl)-propionic acid | 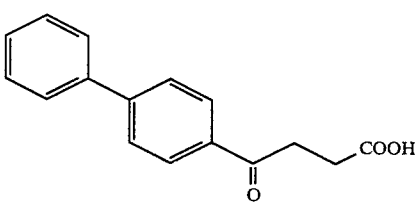 |
| 2-(5-Benzoyl-2-thienyl)-propionic acid | 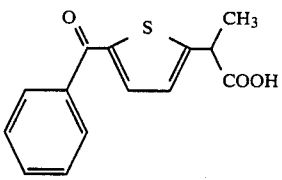 |
| 1-(p-Chlorobenzoyl)-5-methoxy-2-methylindole-3-acetic acid = indometacin | 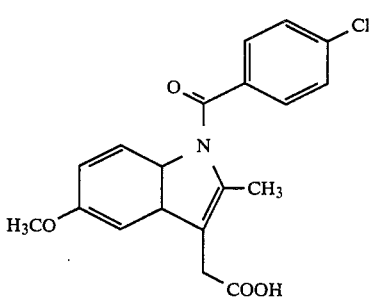 |

-continued 1-(p-Chlorobenzoyl)-5-methoxy-2-
methylindole-3-acetoxyacetic acid = acemetacin

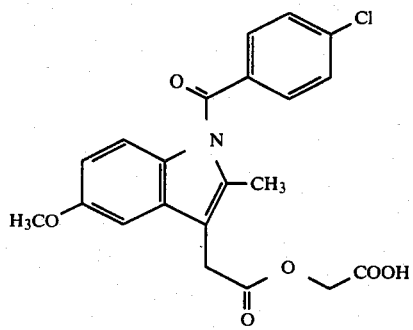

(Z)—5-Fluoro-2-methyl-1-([(3-methyl-
sulphinyl)phenyl]-methylene)-1H—indene-
3-acetic acid

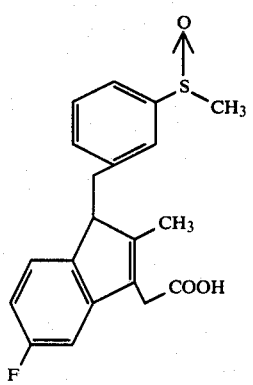

4-Butyl-1,2-diphenyl-3,5-
pyrazolidine-dione = phenylbutazone

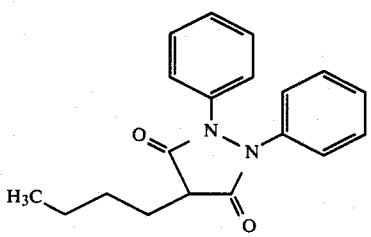

4-(3-Methyl-but-2-enyl)-
1,2-diphenyl-pyrazolidine-
3,5-dione = feprazone

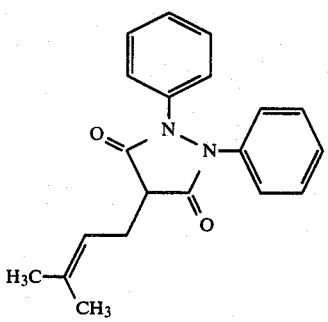

2-(4-Chlorphenyl)-α-methyl-5-
benzoxazoleacetic acid = benoxaprofen

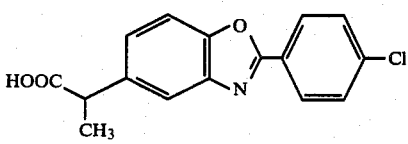

N—(2-thiazolyl)-2-methyl-4-hydroxy-
2H—1,2-benzothiazine-3-carboxamide
1,1-dioxide

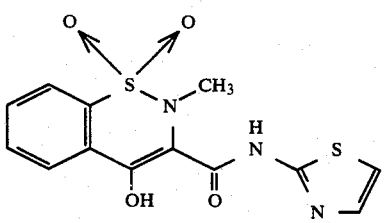

N—(2-pyridinyl)-2-methyl-4-hydroxy-2H—1,2-benzothiazine-3-carboxamide 1,1-dioxide (keto/enole mixture)

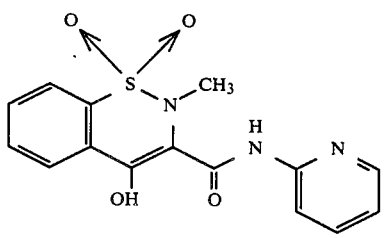

and alkyl esters and substituted alkyl esters thereof.

Either one or more of the abovementioned antiphlogistics of the general formulae I and II can be incorporated into the plasters.

The antiphlogistics can be incorporated into the reservoir layer in an amount of 1–30% by weight, preferably 2–20% by weight. The % by weight given relate to the total reservoir.

Other active substances or cooling or fragrance-releasing substances, preferably methylsalicylate, glycol salicylate, salicylic acid, menthol, peppermint oil, camphor, thymol, Acrinol, scopola extract, chloropeniramine maleate, benzyl nicotinate, capsicum extract, nonylvanillylamide and capsaicin, can also additionally be added to these antiphlogistics.

If necessary, additives and fillers, for example anti-ageing agents, antioxidants and reinforcing fillers, can be added to the plasters according to the invention as long as the gel-like properties are not destroyed.

Known active compound release systems, such as, for example, gels, ointment bases and plasters, release about 0.5–5% of active compound in 7 hours. In contrast, the therapeutic system according to the invention described above releases up to 33% of active compound in 7 hours, with a significantly greater bioavailability. The rate of release of the active compound from the systems according to the invention can be adjusted to almost any desired value by changing the polymer content, the entraining agent or the resin.

The reservoir containing the active compound and the plaster based thereon can be produced, for example, as follows: the plaster bases (polymer, resin and entraining agent) are introduced into a suitable dissolving vessel and are dissolved in benzene, with stirring. A clear to slightly turbid solution results. The active compound component is also dissolved in a suitable solvent, and the solution is added to polymer solution.

The resulting solution containing active compound is applied uniformly to siliconized paper and drawn to a film. The coated paper with the plaster base is dried in air for 24 hours and then kept in a circulating air drying cabinet at 40° C. for 1 hour.

The rates of release of active compound are determined in an absorption model described in more detail in the experimental section.

The invention will be further described with reference to the examples hereinbelow and the accompanying drawings, wherein.

Figure 1:
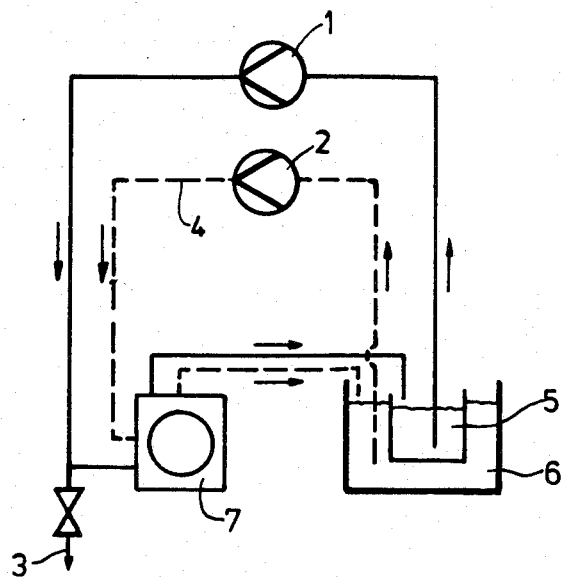
FIG. 1 is a schematic view of an apparatus for testing.

Referring now more particularly to the drawings, in FIG. 1 1 is a hose pump for the acceptor and 2 is a hose pump for heating. The sample is withdrawn at 3 and heating liquid is circulated through line 4. The acceptor medium is 5, 6 is the heating vessel and 7 is the resorption vessel, provided with a membrane.

Figure 2:
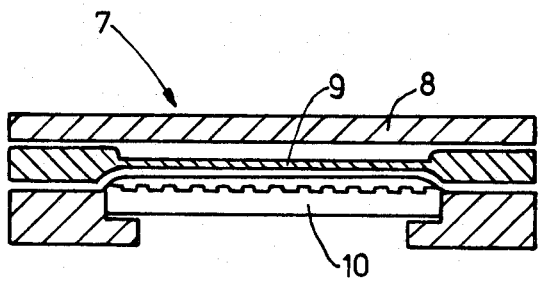
FIG. 2 is a schematic sectional view of the resorption vessel of FIG. 1.

In FIG. 2, the resorption vessel 7 is shown as comprising an opaque cell material 8, a membrane 9 and a viewing window of glass or corrugated plate 10 for the acceptor medium.

In FIGS. 3 to 6 the curves were obtained as described more fully in the examples.

TESTING THE RELEASE IN VITRO OF THE PLASTERS ACCORDING TO THE INVENTION

All the plasters were prepared according to the same basic recipe with an active compound content of 15% (10 or 5%):

Polymer: 40 parts by weight
Entraining agent: 50 parts by weight
Resin: 10 parts by weight
(Solvent: benzine, hexane or a mixture of hexane and toluene)

For this, all the components were dissolved or suspended. Acetone and/or ethanol were chiefly used as the solvents for the active compound.

The active compound was added to the abovementioned solution in amounts of 17.65 parts (that is to say 15% of the finished mixture). These solutions or suspensions were processed to thin films 50–150 μm thick.

Experimental parameters:
acceptor medium: mixture of water, ethanol, PVP and sorbitan fatty acid ester
volume of acceptor medium: 200 ml
temperature of acceptor medium: 35°–36° C.
pump capacity: 14 ml/minutes (apparatus constant)
membrane: the film described in Example 3 of DE-OS (German Published Specification No.) 3,312,735 was used as the membrane
Absorption area: 28.28 cm² (cell constant)

The acceptor medium was brought to the required temperature in a stock vessel and pumped around the absorption cell via tubes. Samples were withdrawn between the pump and the absorption cells. Sample withdrawal was effected at specified intervals of time. In each case, 6 ml of sample were withdrawn and measured by spectrophotometry. The acceptor liquid was not replaced, since this would mean a dilution of the remainder.

CALCULATION OF THE RESULTS

A calibration curve was first recorded for the particular active compound component, with the aid of which the active compound concentration (mg or %) in the individual samples was determined from the extinction values measured for the individual samples. The extinctions were measured by UV spectroscopy.

To calculate the "relative absorption" (proportion of "absorbed" active compound of the total content of the plaster in %), it is necessary to know the amount of active compound used. The active compound content of a defined plaster-size (28.28 cm$^2$) is known from the preparation.

The percentage proportion of "absorbed" active compound expressed as a percentage of the active compound content of the plaster is calculated as follows:

% of "absorbed" active compound up to time $t =$ $$\frac{\frac{\text{mg of active compound in sample} \times V_t}{100} + M_t}{}$$

$$M_t = \sum_{i=0}^{i=n-1} \left( V_s \cdot \frac{C_i}{100} \right)$$

$V_t$ = volume of the acceptor medium at time t in ml
$V_s$ = sample volume in ml
$M_t$ = amount of active compound withdrawn up to time t in mg
n = number of samples at time t
$C_i$ = active compound concentration in the sample [mg/ml]

PLASTER WITH POLYISOBUTYLENE AS THE POLYMER AND ETOFENAMATE AS THE ACTIVE COMPOUND

Example series A

In this series of experiments, polyisobutylenes of various molecular weights were used as the polymer, thinly liquid paraffin was used as the entraining agent and rosin resin ester was used as the resin. The precise composition of the plaster bases is shown in Table 1. The plasters were prepared as described above. The concentration of etofenamate was 15% in the finished, solvent-free plaster. The rates of release are described in FIG. 3. Wr in all the FIGS. 3-6 means the release of active compound.

Figure 3:
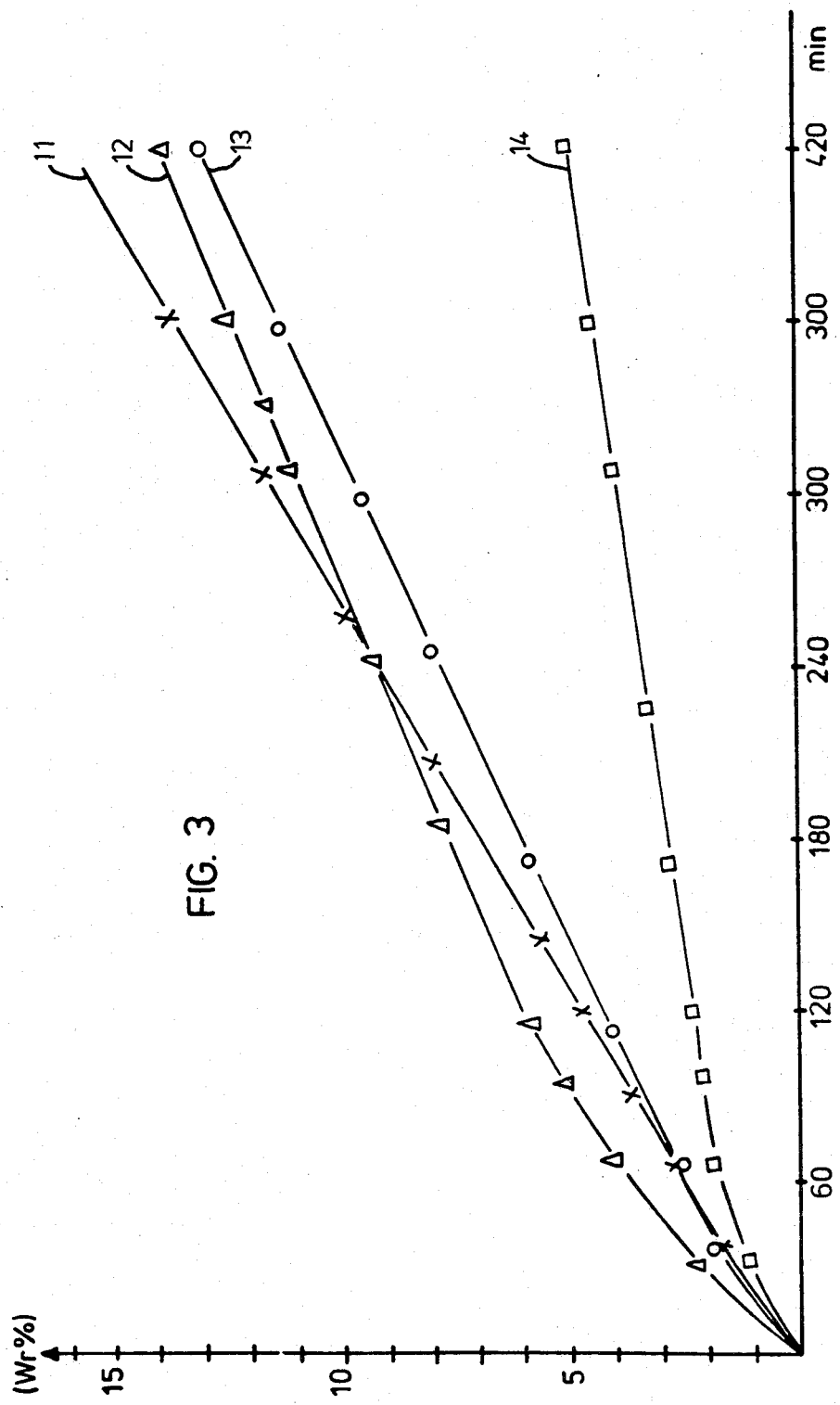
FIGS. 3 to 6 are plots of % release of active compound against time, each figure being a set of plots resulting from changes in a single variable.

The curves in FIG. 3 were obtained as follows:
Curve 11: Pib molecular weight=400,000; No. 102 in Table 1.
Curve 12: Pib molecular weight=40,000; No. 111 in Table 1.
Curve 13: Pib molecular weight=2,800,000; No. 110 in Table 1.
Curve 14: Pib molecular weight=2,700,000; No. 101 in Table 1.

Example series B

Figure 4:
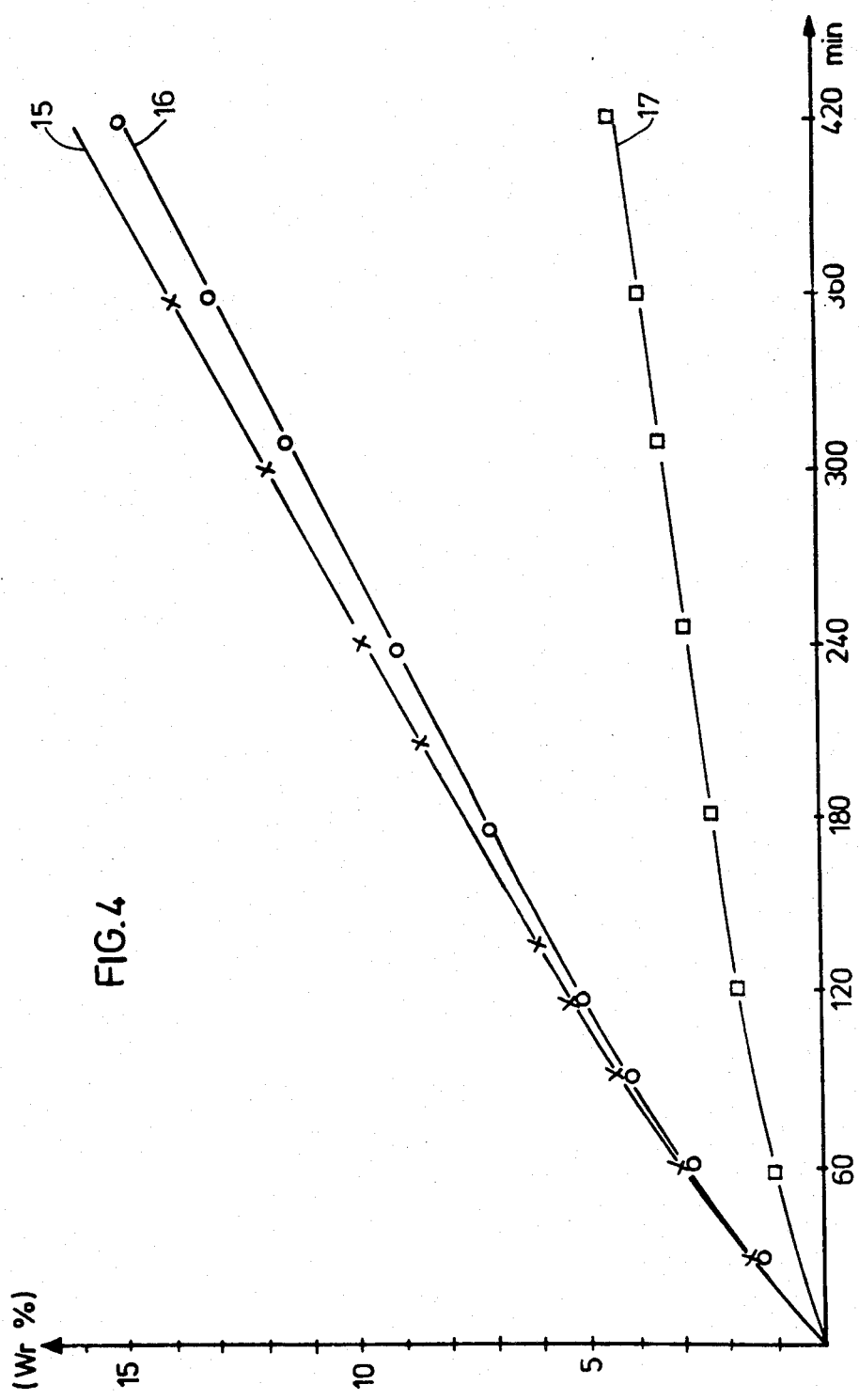

In subsequent experiments, polyisobutylene of molecular weight 400,000 was always used as the polymer component. In the experiments, the paraffin content changed from originally 50 parts to 40 or 60 parts (Table 1). The amounts of polyisobutylene and resin were kept constant. The results are shown in FIG. 4.

The curves in FIG. 4 were obtained for paraffin quantities as follows:
Curve 15: 50 G; No. 102 in Table 1.
Curve 16: 60 G; No. 107 in Table 1.
Curve 17: 40 G; No. 160 in Table 1.

Example series C

Figure 5:
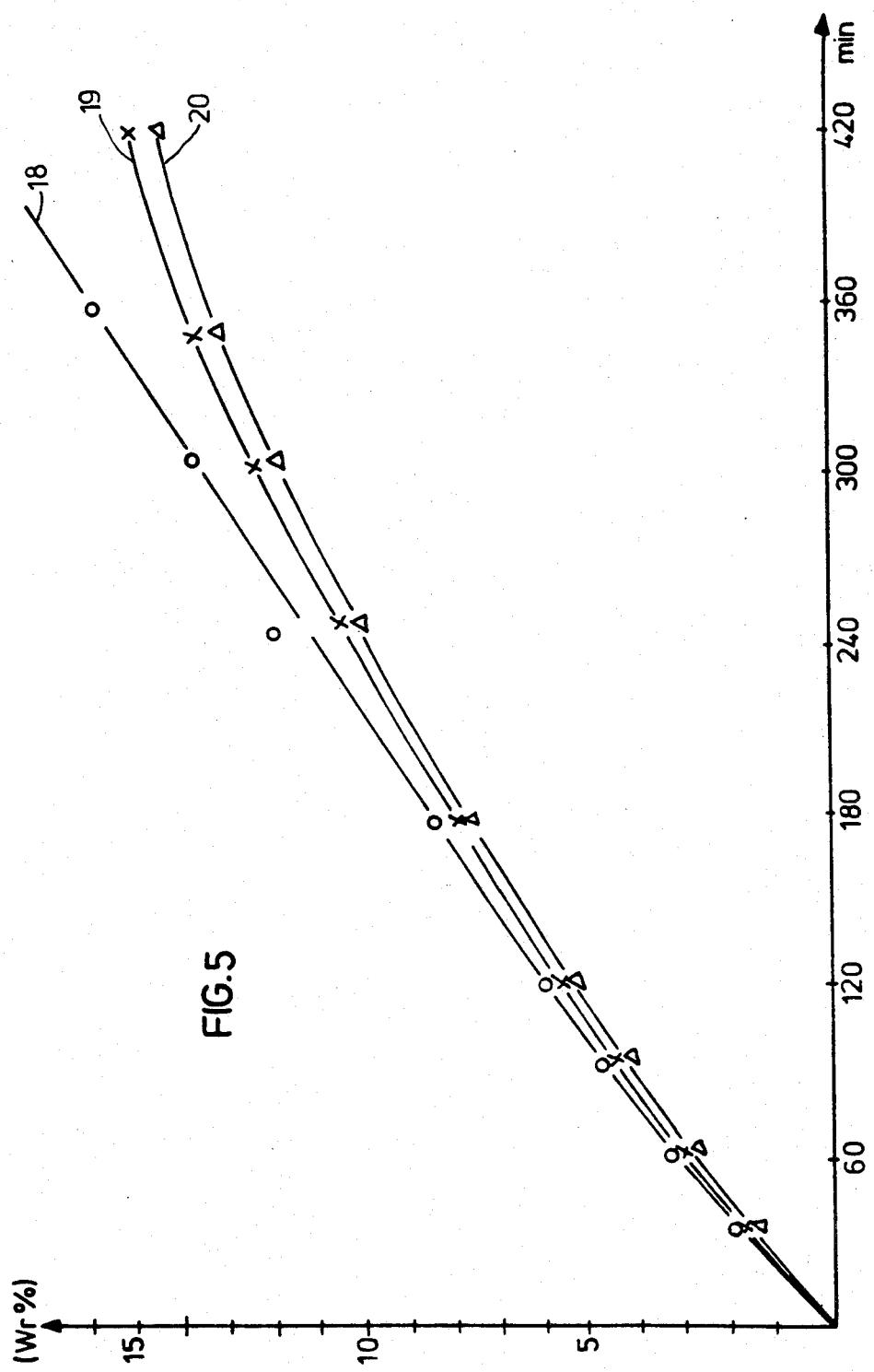

The resin content was halved or doubled, with the contents of polyisobutylene (molecular weight 400,000) and paraffin being constant. Doubling of the resin content caused a slight improvement in the "absorption" from the plaster, whereas halving the resin content resulted in virtually no change (FIG. 5).

The curves in FIG. 5 were obtained for rosin resin ester quantities as follows:
Curve 18: 16 parts of resin; No. 108/Table 1.
Curve 19: 8 parts of resin; No. 107/Table 1.
Curve 20: 4 parts of resin; No. 109/Table 1.

Example series D

Variation of the entraining agent (FIG. 4, Table 2)

Figure 6:
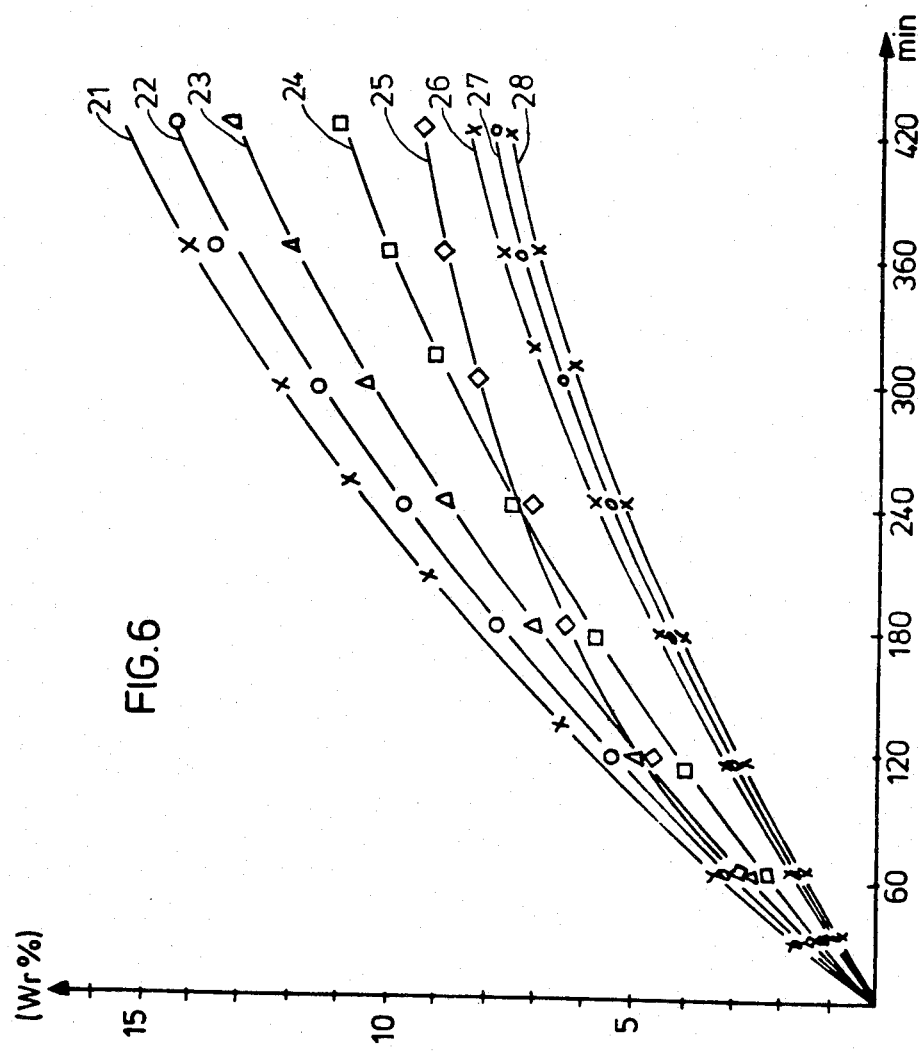

Various entraining agents (instead of paraffin) were investigated in respect of their influence on the rates of release analogously to formulation 102. FIG. 6 shows the results.

The curves in FIG. 6 were obtained using different entraining agents as follows:
Curve 21: Entraining Agent; thinly liquid paraffin; No. 102 in Table 1.
Curve 22: Polybtadiene oil MW 1500; No. 406 in Table 2.
Curve 23: Oleic Acid Decylester; No. 405 in Table 2.
Curve 24: Silicone oil MW 390; No. 403 in Table 2.
Curve 25: Polyisobutylene oil MW 290; No. 401 in Table 2.
Curve 26: Polybutadiene oil MW 3000; No. 407 in Table 2.
Curve 27: Silicone oil MW 600; No. 402 in Table 2.
Curve 28: Isopropyl Myristate; No. 404 in Table 2.

TABLE 1

| No. | Thinly Liquid paraffin/g | Rosin resin ester/g | Polyisobutylene molecular weight/g | | Polyisobutylene molecular weight/g | | Benzine /g | Etofenamate /g | Acetone /g |
|---|---|---|---|---|---|---|---|---|---|
| 101 | 50 | 10 | 1,270,000 | 40 | — | — | 300 | 17.65 | 40 |
| 102 | 50 | 10 | 400,000 | 40 | — | — | 300 | 17.65 | 40 |
| 103 | 50 | 10 | 2,800,000 | 30 | 820 number average | 10 | 300 | 17.65 | 40 |
| 104 | 50 | 10 | 1,270,000 | 30 | 40.000 V.A.* | 10 | 300 | 17.65 | 40 |
| 105 | 50 | 10 | 2,800,000 | 10 | 40.000 V.A.* | 30 | 300 | 17.65 | 40 |
| 106 | 40 | 12 | 400,000 | 48 | — | — | 300 | 17.65 | 40 |
| 107 | 60 | 8 | 400,000 | 32 | — | — | 300 | 17.65 | 40 |
| 108 | 55 | 16 | 400,000 | 29 | — | — | 300 | 17.65 | 40 |
| 109 | 62.5 | 4 | 400,000 | 33.5 | — | — | 300 | 17.65 | 40 |
| 110 | 50 | 10 | 2,800,000 | 40 | — | — | 600 | 17.65 | 40 |
| 111 | 50 | 10 | 40,000 | 40 | — | — | 300 | 17.65 | 40 |

TABLE 1-continued

| No. | Thinly Liquid paraffin/g | Rosin resin ester/g | Polyisobutylene molecular weight/g | Polyisobutylene molecular weight/g | Benzine /g | Etofenamate /g | Acetone /g |
|---|---|---|---|---|---|---|---|
| 115 | 50 | 10 | 400,000  40 | — | 300 | 5.26 | 40 |

*V.A. denotes viscosity average

TABLE 2

| No. | Liquid component Type | /g | Rosin resin ester/g | Polyisobutylene molecular weight 400,000/g | Benzine /g | Etofenamate /g | Acetone /g |
|---|---|---|---|---|---|---|---|
| 401 | Polyisobutylene molecular weight 820 | 50 | 10 | 40 | 300 | 17.65 | 40 |
| 402 | Polydimethylsiloxane molecular weight about 600 | 50 | 10 | 40 | 300 | 17.65 | 40 |
| 403 | Polydimethylsiloxane molecular weight 390 | 50 | 10 | 40 | 300 | 17.65 | 40 |
| 404 | Isopropyl myristate | 50 | 10 | 40 | 300 | 17.65 | 40 |
| 405 | Decyl oleate | 50 | 10 | 40 | 300 | 17.65 | 40 |
| 406 | Polybutadiene oil molecular weight 1,500 | 50 | 10 | 40 | 300 | 17.65 | 40 |
| 407 | Polybutadiene oil molecular weight 3,000 | 50 | 10 | 40 | 300 | 17.65 | 40 |

DESCRIPTION OF THE PREPARATION

The active compound release systems according to the invention were prepared as follows: the mixture of polymer, resin and entraining agent were pre-kneaded in a Z-kneader at a temperature of 120° to 150° C. When the mass was a homogeneous melt, the active compound was incorporated homogeneously, while gassing with nitrogen. The melt containing active compound was applied to the carrier film (kneader).

The active compound release systems according to the invention were also dissolved in a solvent mixture, applied to the carrier film and then dried (solution).

EXAMPLE 1 (solution)

Polyisobutylene of molecular weight 400,000: 40.00 g
Thinly Liquid paraffin oil: 50.00 g
Rosin resin ester: 10.00 g
Etofenamate: 17.65 g
Release: about 15% after 6 hours.

EXAMPLE 2 (solution)

Polyisobutylene of molecular weight 40,000: 40.00 g
Thinly liquid paraffin oil: 50.00 g
Rosin resin ester: 10.00 g
Etofenamate: 17.65 g
Release: about 14% after 6 hours.

EXAMPLE 3 (kneader)

Polyisobutylene of molecular weight 400,000: 40.00 g
Polybutadiene oil of molecular weight 1,500: 50.00 g
Rosin resin ester: 10.00 g
Etofenamate: 17.65 g
Release: about 14% after 6 hours.

EXAMPLE 4 (kneader)

Polyisobutylene of molecular weight 400,000: 40.00 g
Decyl oleate: 50.00 g
Rosin resin ester: 10.00 g
Etofenamate: 17.65 g
Release: about 13% after 6 hours.

EXAMPLE 5 (kneader)

Polyisobutylene of molecular weight 400,000: 40.00 g
Silicone oil: 50.00 g
Rosin resin ester: 10.00 g
Etofenamate: 17.65 g
Release: about 9.5% after 6 hours.

EXAMPLE 6 (solution)

Polyisobutylene of molecular weight 400,000: 32.00 g
Thinly liquid paraffin: 60.00 g
Rosin resin ester: 8.00 g
Etofenamate: 17.65 g
Release: about 13.5% after 6 hours.

EXAMPLE 7 (solution)

Polyisobutylene of molecular weight 400,000: 29.00 g
Thinly liquid paraffin: 55.00 g
Rosin resin ester: 16.00 g
Etofenamate: 17.65 g
Release: about 15.5% after 6 hours.

EXAMPLE 8 (solution)

Polyisobutylene of molecular weight 400,000: 33.50 g
Thinly liquid paraffin: 62.50 g
Rosin resin ester: 4.00 g
Etofenamate: 17.65 g
Release: about 14.5% after 6 hours.

EXAMPLE 9 (solution)

Polyisobutylene of molecular weight 400,000: 40.00 g
Thinly liquid paraffin: 50.00 g
Rosin resin ester: 10.00 g
Etofenamate: 5.26
Release: about 32.5% after 6 hours.

EXAMPLE 10 (solution)

Polyisobutylene of molecular weight 400,000: 40.00 g
Polybutadiene oil of molecular weight 1,500: 50.00 g
polyterpene resin from α-pinene: 10.00 g
Etofenamate: 17.65 g
Release: about 16% after 6 hours.

EXAMPLE 11 (solution)

Polyisobutylene of molecular weight 400,000: 40.00 g
Thinly liquid paraffin: 50.00 g
Polyterpene resin from β-pinene: 10.00 g
Etofenamate: 17.65 g
Release: about 16.5% after 6 hours.

EXAMPLE 12 (kneader)

Polyisobutylene of molecular weight 400,000: 40.00 g
Polybutadiene oil of molecular weight 1,500: 50.00 g
Modified glycerol ester of rosin: 10.00 g
Etofenamate: 5.26 g
Release: about 33% after 6 hours.

EXAMPLE 13 (solution)

Polyisobutylene of molecular weight 400,000: 40.00 g
Thinly liquid paraffin: 50.00 g
Modified glycerol ester of rosin: 10.00 g
Ketoprofen: 5.26 g
Release: about 20% after 6 hours.

EXAMPLE 14 (solution)

Polyisobutylene of molecular weight 400,000: 40.00 g
Thinly liquid paraffin: 50.00 g
Polyterpene resin from α-pinene: 10.00 g
Acemetacin: 17.65 g
Release: about 12% after 6 hours.

It will be understood that the specification and examples are illustrative but not limitative of the present invention and that other embodiments within the spirit and scope of the invention will suggest themselves to those skilled in the art.

We claim:

1. In a therapeutic system including a covering layer which is essentially impermeable to an active compound, an active compound reservoir layer and a protective layer which can be pulled off and which is essentially impermeable to the active compound, the improvement comprising the reservoir layer containing about 1–30% of active compound, about 30–60% by weight of a polymer selected from the group consisting of polyisobutylenes, copolymers of polyisobutylenes and mixtures thereof, 30–60% by weight of an entraining agent selected from the group consisting of oils, fatty acid esters, triglycerides, alcohols, fatty acids and mixtures thereof and 2–40% by weight of a resin selected from the group consisting of rosin, dehydrogenated rosin, glycerol esters of dehydrogenated rosin, glycerol esters of rosin gum, hydrogenated rosin, glycerol esters of hydrogenated rosin, pentaerythritol esters of hydrogenated rosin, methyl esters of hydrogenated rosin, polymerized rosin, glycerol esters of polymerized rosin, terpene resins, coumarone/indene resins, hydrogenated petroleum resins, rosin modified by maleic anhydride, $C_5$-petroleum resins, half-esters of styrene/maleic acid copolymers, and mixtures thereof, in addition to the active compound.

2. A therapeutic system comprising a plaster for administration of an active compound through the skin, and comprising a covering layer, a reservoir layer which contains the active compound and also contains a polymer, an entraining agent selected from the group consisting of oils, fatty acid esters, triglycerides, alcohols, fatty acids and mixtures thereof, a resin, said resin selected from the group consisting of rosin, dehydrogenated rosin, glycerol esters of dehydrogenated rosin, glycerol esters of rosin gum, hydrogenated rosin, glycerol esters of hydrogenated rosin, pentaerythritol esters of hydrogenated rosin, methyl esters of hydrogenated rosin, polymerized rosin, glycerol esters of polymerized rosin, terpene resins, coumarone/indene resins, hydrogenated petroleum resins, rosin modified by maleic anhydride, $C_5$-petroleum resins and half-esters of styrene/maleic acid copolymers, and mixtures thereof, and a protective layer which can be pulled off, wherein the polymer of the reservoir layer containing active compound is selected from the group consisting of polyisobutylene and a copolymer of isobutylene with 1–5 mol% of conjugated diene having a molecular weight distribution $m_w/M_n$ of 1.5–3.5 and a viscosity average molecular weight of 30,000 to 4,000,000, the reservoir containing 2–30% by weight of an antiphlogistic as active compound.

3. A therapeutic system according to claim 1, wherein the polymer comprises polyisobutylene with a viscosity average molecular weight of 50,000–1,000,000 g/mol.

4. A therapeutic system according to claim 1, wherein the polymer comprises a copolymer of isobutylene with 1–5 mol % of conjugated diolefin.

5. A therapeutic system according to claim 1, wherein the entraining agent comprises at least one of paraffin oil and liquid polybutadiene oil.

6. A therapeutic system according to claim 1, wherein the active compound is selected from the group consisting of antiphlogistics of the formula

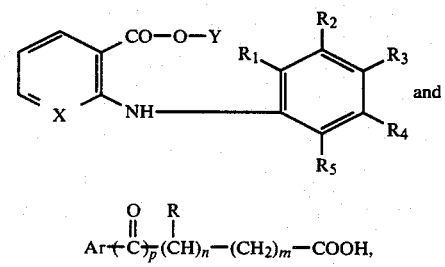

$$Ar\underset{p}{(C} \underset{\parallel}{\overset{O}{}})\underset{n}{(CH)}\underset{}{\overset{R}{}}-(CH_2)_m-COOH,$$

and esters and amides thereof, in which
$R_1$–$R_5$ each independently is hydrogen, halogen, lower alkyl or substituted alkyl,
X is N or CH,
Y is hydrogen, a metal ion, alkyl or substituted alkyl,
R is hydrogen, lower alkyl or substituted alkyl,
Ar is aryl, heteroaryl, substituted aryl or substituted heteroaryl,
n and m each is an integer and together total zero, 1 or 2, and
p is zero or 1,
with the proviso that Ar is not aryl or heteroaryl if n, m and p each is zero.

7. A plaster according to claim 2, wherein the entraining agent comprises isopropyl myristate.

8. A system according to claim 1, wherein the active compound is etofenamat.

9. A system according to claim 1, wherein the active compound is ketoprofen.

10. A system according to claim 1, wherein the active compound is acematacin.

11. A system according to claim 1, wherein the active compound is indoprofen.

12. A system according to claim 1, wherein the active compound is indometacin.

UNITED STATES PATENT AND TRADEMARK OFFICE
CERTIFICATE OF CORRECTION

PATENT NO. : 4,623,346

DATED : Nov. 18, 1986

INVENTOR(S) : Miklos von Bittera, et al.

It is certified that error appears in the above-identified patent and that said Letters Patent is hereby corrected as shown below:

| | |
|---|---|
| Col. 4, line 18 | Delete "nicotine" and substitute --nicotinic-- |
| Col. 5, line 15 | Delete second formula and substitute 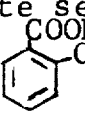 |
| Col. 5, line 45 | Delete "2-(4-chlorophenyl)-αacid" and substitute --phenylacetic acid-- |
| Col. 5, line 59 | Correct spelling of --toluoyl-- |

Signed and Sealed this

Twenty-first Day of April, 1987

Attest:

DONALD J. QUIGG

Attesting Officer

Commissioner of Patents and Trademarks